United States Patent [19]

Baxter-Lowe et al.

[11] Patent Number: 5,468,611
[45] Date of Patent: Nov. 21, 1995

[54] METHOD FOR HLA TYPING

[75] Inventors: Lee A. Baxter-Lowe, New Berlin; Jack A. Gorski, Mukwonago, both of Wis.

[73] Assignee: The Blood Center Research Foundation, Inc., Milwaukee, Wis.

[21] Appl. No.: 45,530

[22] Filed: Apr. 8, 1993

Related U.S. Application Data

[63] Continuation of Ser. No. 544,218, Jun. 27, 1990, abandoned.
[51] Int. Cl.⁶ ............................. C12Q 1/68; C12P 19/34
[52] U.S. Cl. .................................... 435/6; 435/91.2
[58] Field of Search .................... 435/6, 91, 91.2

[56] References Cited

U.S. PATENT DOCUMENTS

| | | | |
|---|---|---|---|
| 4,582,788 | 4/1986 | Erlich | 435/6 |
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,835,098 | 5/1989 | Orr et al. | 435/6 |

FOREIGN PATENT DOCUMENTS 1205400   6/1986   Canada.

OTHER PUBLICATIONS

Fielder et al., *Human Immunology*, vol. 25, pp. 75–85 (1989).
Angelini et al., *Proc. Natl. Acad. Sci. USA*, vol. 83, pp. 4489–4493 (1986).
Scharf et al., *Science*, vol. 233, pp. 1076–1078.
Cox et al., *Am. J. Hum. Gen.*, vol. 43, No. 6, pp. 954–963, 1988.
Tiercy et al. *Proc. Natl. Acad. Sci. USA.*, vol. 85, pp. 198–202, 1988.
Tiercy et al., *Hum. Immunol.*, vol. 24, pp. 1–14 (1989).
Bugawan et al., *J. Immunol.*, vol. 141, No. 12, pp. 4024–4030, 1988.
Gyllensten et al., *Proc. Natl. Acad. Sci. USA*, vol. 85, pp. 7652–7656, 1988.
Ronningen et al., *Human Immunology*, vol. 24, pp. 165–173, 1989.
Ucla et al., *J. Clin. Invest.*, vol. 80, pp. 1155–1159 (1987).
Le Gall et al. *Proc. Natl. Acad. Sci. USA*, vol. 83, pp. 7836–7840 (1986).
Baxter–Lowe et al., *J. Clin. Invest.*, vol. 84, pp. 613–618 (1989).
Saiki et al., *Nature*, vol. 324, No. 13, pp. 163–166 (1986).
*Human Immunology*, vol. 23, No. 2, 1988, pp. 78–81.
Gorski, *Human Immunology*, vol. 24, pp. 145–149 (1989).
Gorski et al., *Nature*, vol. 322, No. 6074, pp. 67–70 (1986).
Saiki, *Proc. Natl. Acad. Sci. USA*, vol. 86, pp. 6230–6234 (1989).
Vaughan, *Tissue Antigens*, vol. 36, pp. 149–155, 1990.
Gao et al., *Human Immunology*, vol. 27, pp. 40–50 (1990).
So et al., *J. of Immuno.*, vol 139, pp. 3506–3511 (1986).
Horn et al., *Proc. Natl. Acad. Sci. USA.*, vol. 85, pp. 6012–6016 (1988).
Mullis et al., *Methods in Enzymology*, vol. 155, pp. 335–350 (1987).
Saiki et al., *Science*, vol. 230, pp. 1350–1354 (1985).
Kohonen–Corish et al., *Hum Immunol.*, vol. 15, pp. 263–271 (1986).
Xiaojiang Gao et al., *Hum. Immunol.*, vol. 27, pp. 40–50 (1990).
Lanchbury et al., *Hum. Immunol.*, vol. 27, pp. 136–144 (1990).
Ash et al., *N. Engl. J. Med.*, vol. 322, pp. 485–494 (1990).

*Primary Examiner*—Mindy B. Fleisher
*Attorney, Agent, or Firm*—Foley & Lardner

[57] ABSTRACT

A method for HLA typing by amplification of a sample followed by sequence-specific oligonucleotide hybridization with a labelled oligonucleotide probe provides for both positive and negative controls. Control sequences representing known allelic polymorphisms at the locus in question are subjected to the labelled probe along with the sample. This method reduces errors and improves the chance of obtaining a successful tissue match, as is vital in the case of tissue transplants, particularly bone marrow transplants. Probes and PCR primers useful in HLA-DR typing are also provided.

16 Claims, 1 Drawing Sheet

A

|  | D70 | A70 | E58 | L30 |
|---|---|---|---|---|
| CHILD | — |  | — | — |
| MOTHER |  |  |  | — |
| FATHER | — |  | — |  |
| AUNT |  |  | — |  |
| M. GRANDMOTHER |  |  | — |  |
| 1/2 SIBLING |  |  | — |  |
| P. GRANDMOTHER |  |  | — |  |
| P. GRANDFATHER | — |  | — |  |

B

| DR TYPE | SOURCE | D70 | A70 | E58 | L30 |
|---|---|---|---|---|---|
| DR 1 | WT100 |  |  |  |  |
| DR16, W21 | WJR |  | — |  |  |
| DR15, W2 | AMAI |  | = |  |  |
| DR16, W22 | RML |  | — |  |  |
| DR3, 52a | STEIN |  |  |  |  |
| DR4, W4 | WTS |  |  |  |  |
| DR4, W10 | YAR |  |  |  |  |
| DR4, W14 | PE 117 |  |  |  |  |
| DR11, W5, 52b | SWEIG | — |  | — |  |
| DR13, W19, 52c | EMJ |  |  |  |  |
| DR14, W9, 52b | TEM |  |  |  |  |
| DR7, W17 | MOU |  |  |  | — |
| DR4, 8 | JON | — |  |  |  |
| DR9, W23 | DKB |  |  |  |  |

METHOD FOR HLA TYPING

This is a continuation of U.S. Ser. No. 07/544,218 filed on Jun. 27, 1990 abandoned.

FIELD OF THE INVENTION

The Invention relates to a method of typing human leukocyte antigens for purposes of, for example, tissue matching, identification or disease susceptibility. In particular, this invention relates to HLA-DR typing, and methods and probes useful for HLA-DR typing.

BACKGROUND OF THE INVENTION

The major histocompatibility complex of humans (denoted HLA-human leukocyte antigen) is a cluster of genes occupying a region located on the sixth chromosome. The polymorphic proteins encoded by the HLA region have been designated HLA-A,-B,-C,-DR,-DQ, and -DP. HLA-A, -B, and -C consist of a single polymorphic chain. HLA-DR, -DQ, and -DP proteins contain two polymorphic chains, designated alpha and beta. These D-region proteins are encoded by loci designated DRA, DRB1, DRB3, DRB4, DQA1, DQB1, DPA1, and DPB1.

The products encoded by the polymorphic HLA loci are most commonly typed by serological methods. Such typing is used in paternity determinations, transplant and transfusion histocompatibility testing, blood component therapy, anthropological studies and in disease association correlation to diagnose diseases or predict susceptibility to diseases. The major drawbacks to such HLA typing, particularly of the Class II loci, are the complexity of the sera and the lack of widespread availability of standard sera necessary to conduct the tests. In addition, since serological typing is based on reactions of sera with the HLA gene products, it is not useful for HLA typing for HLA-deficient individuals in whom HLA products are reduced or absent.

Serological or cellular HLA typing techniques require the presence of detectable levels of HLA proteins on the surface of lymphocytes. In some cases (e.g., HLA-deficient SCID or cellular depletion due to chemotherapy), the levels of the HLA proteins or number of available cells are inadequate to achieve reliable HLA typing. Another limitation of traditional typing methods is the inability to resolve all functionally important HLA alleles. These circumstances have prompted the development of methods for analysis of HLA polymorphism at the genetic level, as described in Bidwell, J., 1988, *Immunology Today* 9:18–23, and Angelini et al., 1986, *Proc. Natl. Acad. Sci. USA*, 83:4489–4493.

Non-serological HLA typing methods have been proposed to overcome drawbacks with serological typing. One such method involves the use of DNA restriction fragment length polymorphism (RFLP) as a basis for HLA typing. See Erlich U.S. Pat. No. 4,582,788, issued Apr. 15, 1986. Polymorphism detected by this method is located in both coding and noncoding sequences of the genome. Therefore, RFLP often does not directly measure functional polymorphism, but relies upon linkage disequilibrium between polymorphism in non-coding regions and the coding region. RFLP analysis has been used for typing an HLA-deficient severe combined immunodeficiency (SCID) patient, but its utility as a routine method is limited by laborious procedures, inadequate resolution of alleles, and difficulty in interpreting data for certain combinations of alleles.

Some RFLP and similar typing methods utilize labelled obligonucleotides to identify specific HLA and DNA sequences. In particular, the use of oligonucleotide probes have been found advantageous in HLA-DR typing in identifying variant genes encoding products which are not detectable serologically. See Angelini et al., above, Scharf et al., *Science*, Vol. 233, No. 4768, pp. 1076–1078, Cox et al., *Am. J. Hum. Gen.*, 43:954–963, 1988, Tiercy et al., *Proc. Natl. Acad. Sci. USA*, Vol. 85, pp. 198–202, 1988, and Tiercy et al., *Hum. Immunol.* 24, pp. 1–14 (1989). Sequence-specific oligonucleotide probe hybridization (SSOPH) can discriminate single base pair mismatches, which is equivalent to detecting a single amino acid polymorphism in HLA proteins.

The polymerase chain reaction (PCR) process, as described in Mullis U.S. Pat. No. 4,683,202, issued Jul. 28, 1987, allows the amplification of genomic DNA and has given rise to more convenient HLA typing procedures. HLA-DQ alpha and HLA-DP alpha and beta genes have been amplified, and then sequenced or hybridized with oligonucleotide probes. See Saiki et al., *Nature*, Vol. 324, pp. 163–166, 1986, Bugawan et al., *J. Immunol.*, Vol. 141, No. 12, pp. 4024–4030, 1988, and Gyllensten et al., *Proc. Natl. Acad. Sci. USA*, Vol. 85, pp. 7652–7656, 1988. However, these methods have limited reliability due to the tendency of the probes to bind with greater or lesser specificity depending on the reaction conditions employed. The present invention addresses the latter problem and provides certain specific probes and primers useful in HLA-DR typing.

The invention further concerns the use of HLA typing methods for tissue matching, especially for purposes of tissue transplantation. Bone marrow transplants, in particular, are the treatment of choice for certain immunodeficiency syndromes and hematological disorders. The success of bone marrow transplantation is influenced by the degree of HLA compatibility between recipient and donor. However, aberrant HLA expression sometimes makes it difficult, if not impossible, to determine the patient's HLA type by standard serological and cellular techniques.

Successful bone marrow transplantation depends on the degree of HLA matching between donor/recipient pairs. This results from the physiological role of human lymphocyte antigens in self-restriction of cellular interactions during and immune response. See Schwartz, *Ann. Rev. Immunol.* 3:27–261, 1985. If polymorphic residues in the HLA proteins are mismatched, the immune system may recognize the cells bearing the mismatched HLA as foreign. The consequences of such mismatching include graft-versus-host disease (GVHD), graft rejection, and failure to reconstitute a competent immune system. See Hows, *Bone Marrow Transplantation*, 1:259–264. These problems are minimized by selection of HLA-matched siblings as donors. Unfortunately, this option is available for only about 30–40% of patients who could benefit from a bone marrow transplant. In the remaining patients (60–70%), HLA typing with high resolving power is necessary for selection of an optimally matched, unrelated donor.

More than 40 variant HLA-DR beta alleles have been identified among the population, and more are being identified on an ongoing basis. It has been suggested that, within the population, HLAs may exist as numerous combinations of a group of polymorphic sequences, rather than a limited number of discrete alleles. The present invention provides a comprehensive process for HLA typing which overcomes many problems associated with serological typing methods, for example, the requirement for HLA-expression, viable cells, and limitations in resolving certain alleles. The invention further provides a method of tissue matching which has provided superior results in the context of bone marrow transplantation.

SUMMARY OF THE INVENTION

The present invention provides an improved method for HLA typing which can be used together with known typing techniques to assess HLA matching between a patient and potential bone marrow donors. Such a method involves successive steps of specifically amplifying DNA from the subject and detecting polymorphic residues by sequence-specific oligonucleotide probe hybridization (SSOPH), as in the prior art. However, prior processes of this type have failed to recognize that, in routine analysis, identification errors can occur as a result of subtle variations in hybridization or wash conditions, particularly when it is necessary to distinguish among closely similar sequences. For example, a given probe may under some conditions hybridize both with the target sequence and with another, closely similar sequence, causing a false positive if the latter is identified as the former.

To avoid such errors, the HLA typing method of the invention involves a step of hybridizing the probe used on the sample with a series of known control DNA sequences representing the consensus sequence and other (preferably all) sequences representing all known alleles at the positions targeted by the probe. In this manner false positives can be readily identified. False negatives can be detected by including the sequence targeted by the probe as one of the controls. The fact that false positives commonly occur in HLA probe hybridizations has gone unrecognized in methods based on known HLA typing methods, which provide no such controls.

More specifically, a method for HLA typing includes steps of:

(a) amplifying an HLA sequence of DNA of a human subject;

(b) bringing a labelled oligonucleotide probe that recognizes an allelic polymorphism at an HLA locus into contact with a sample of the amplified HLA sequence and control sequences representing known alleles at the selected HLA locus under hybridizing conditions, one of the control sequences preferably having the sequence of the allelic polymorphism the probe hybridizes with;

(c) detecting the formation of a DNA duplex between the labelled probe and the HLA sample sequence and the control sequences; and (d) detecting a false positive by observation of hybridization between the probe and two or more of the control sequences, or a false negative by observation of non-hybridization between the probe and the control sequence having the sequence of the allelic polymorphism the probe hybridizes with;

optionally (e) repeating steps (a) to (d) with different labelled probes and additional samples of the HLA sequence and corresponding control sequences as needed to identify differences between the HLA sequence and a corresponding HLA consensus sequence; and optionally (f) comparing the HLA sequence with a set of known HLA alleles to determine if the allele in the sample corresponds to one or more of the alleles of the set. Such a method has proven particularly useful in analyzing highly polymorphic HLA-DR beta sequences.

The HLA typing method according to the invention is particularly useful as part of a method for tissue matching. HLA genes are selectively amplified from DNA isolated from the patient, family members, and prospective unrelated donors, and polymorphic residues in the amplified DNA are identified by SSOPH. The probes used are selected in order to determine which HLA sequences are present in the patient. This information can then be used for tissue matching (e.g., bone marrow transplantation), identification (forensic or paternity testing) and disease susceptibility, e.g. for purposes of preventative therapy or insurance.

The invention further provides a method of tissue matching for bone marrow transplantation purposes which has proven highly effective in screening potential bone marrow donors for HLA compatibility with the patient. Such a method involves HLA typing a potential tissue transplant recipient and a pool of potential donors, and then performing the transplant using the donor which most closely matches the HLA type of the recipient. Bone marrow transplants are particularly difficult because the transplanted bone marrow itself produces leukocytes, so that both tissue rejection and graft-versus-host disease can cause the transplant to fail. According to one aspect of the invention, it has been found that an HLA-DR beta match between recipient and donor is particularly important to obtaining a successful transplant in cases wherein T-cells are transplanted together with bone marrow.

According to a modified form of the invention, specific sequences of HLA and other genetic sequences exhibiting similar polymorphism may be detected by sequence specific amplification (SSA). In essence, the primers used to carry out the amplification are chosen to represent sequences that distinguish one allele from another. As a result, the allele is detected if amplification occurs, and is absent if no amplification occurs. This technique eliminates the need to conduct sequence-specific hybridization in order to distinguish among closely similar alleles.

BRIEF DESCRIPTION OF THE DRAWING

The invention will be further described with reference to the accompanying drawings which relate to the example below, wherein.

DETAILED DESCRIPTION

Figures 1, 2, 3:
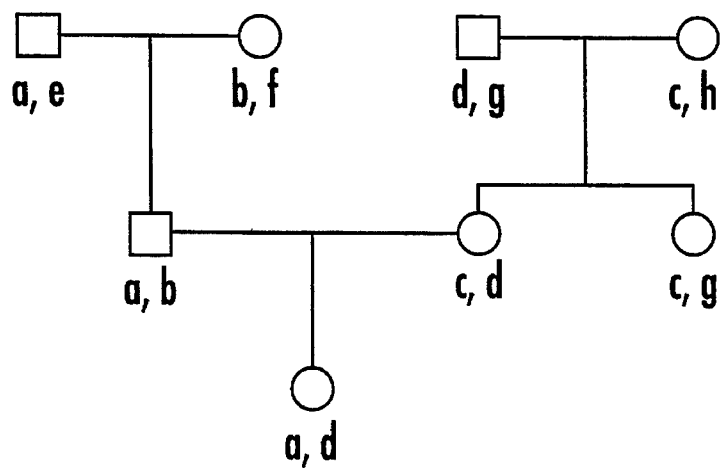
FIG. 1 is a diagram of an autoradiogram of an SSOPH analysis according to the invention for a subject (child) and family members. Each row shows hybridization results derived from the source of the DNA that is listed at the left. The DNA in each column has been hybridized with the oligonucleotide probe indicated at the top of the column.
FIG. 2 is a diagram of an autoradiogram which shows hybridization controls using DNA derived from well characterized cells for which the name, DR and Dw type are given at left. All cells except JON and DKB are from the core LCL panel from the Tenth International Histocompatibility Workshop. Oligonucleotide probes used in hybridizations are indicated at the top of each column.
FIG. 3 is a schematic diagram of haplotypes for the patient of the example below and family members showing the patient's pedigree and the associated serological specifities given in Table 8.

The present invention utilitzes DNA amplification and sequence-specific oligonucleotide probe hybridization (SSOPH) to accomplish HLA matching, especially for purposes of tissue transplantation, e.g., in the selection of donors for bone marrow transplantation. One important advantage provided by the method of the invention is latitude in quality, quantity and source of tissue for analysis. This will be valuable in numerous circumstances in which it is not possible to obtain a sufficient number of normal lymphocytes (e.g., as a result of HLA deficiency or chemotherapy) to achieve reliable HLA typing by conventional methods. A second major advantage of SSOPH is explicit definition of alleles. Serological reagents generally cannot provide discrimination between all known HLA alleles. In contrast, SSOPH detects polymorphisms that predict differences at the level of single amino acid residues. Such micropolymorphism can influence the outcome of transplantation, and thus matching at this level is highly useful.

Oligonucleotide probes according to the invention comprise a sequence of nucleotides that will hybridize with the sequence of interest, which sequence is labelled with a labelling substance, such as $^{32}$P. In general, such probes will contain from about 12 to 25 nucleotides. A probe containing at least 12 nucleotides is usually required to achieve efficient hybridization to a unique site in the DNA. Probe sequences longer than 25 nucleotides are generally impractical because it becomes too difficult to resolve single base pair mismatches.

Table 1 sets forth nucleotide sequences for HLA-DR beta alleles, and Table 2 sets forth the corresponding amino acid sequence for HLA-DR beta alleles at loci B1, B3 and B4. Differences in the amino acids encoded from the consensus sequence are indicated in the same manner as in Table 1:

TABLE 1

```
          6    R   F   L   E   Q   X  10 K   S   E   C   H   F   F   N   G  20 T   E   R   V   R   F          L
DR cons       CACGTTTCTTGGAGCAGx xTAAGTCTGAGTGTCATTTCTTCAATGGGACGGAGCGGGTGCGGTTCCT
DRw52a        -----------------T-CG-------------------------------------------
DRw52b.1      -----------------T-CT-------------------------------------------
DRw52b.2      -----------------T-CT-------------------------------------------
DRw52b.3      -----------------T-CT-------------------------------------------
DRw52c        -----------------T-CT-------------------------------------------
Drw12a,b      -----------------T-CTC----CGG-----------------------------A-----
DR3a          -----------------T-CTC----C-------------------------------A-----
DR3b          ----------------------------------------------------------------
DR5a,b,c,e    ------------------T-CTC---C-------------------------------------
DR5d          ------------------T-CTC---C-------------------------------------
NEW 1         ------------------T-CTC---C-------------------------------------
DRw6a         ------------------T-CTC---C-------------------------------------
DRw6c         ------------------T-CTC---C-------------------------------------
DRw6b         ------------------T-CTC---C-------------------------------------
DRw6d         ------------------T-CTC---C-------------------------------------
DRw6e         ------------------T-CTC---C-------------------------------------
DRw8a&b       ------------------T-CTC---C-GG----------T-----------------------
DRw8c         ------------------T-CTC---C-GG----------T-----------------------
NEW 2         ------------------T-CTC---C-GG----------T-----------------------
DRw8d         ----------------------------------------------------------------
DRw53a        -------------------GC-----G-----------C-------------A---T--AA---
DRw53b        -------------------GC-----G-----------C-------------A------AA---
DRw53c        -------------------GC-----G-----------C-------------A---CT-AA---
DR4a-e        -------------------GT----ACA----------C-------------------------
DR4F          -------------------GT----ACA----------C-------------------------
DR7          C---TG-------------GG----A-A----------C-------------A---------AT-
DR9          ---A---------------GA----A-T-----------------------------------
DR2a B3      -C-----------------GA----A-------------------------------------
DR2b B3      -C-----------------GA----A-------------------------------------
DR2c B3      -C-----------------GA----A-------------------------------------
DR2a B1      ---TG--------------CC---AGG------------------------------------
DR2b B1      ---TG--------------CC---AGG------------------------------------
DR2c B1      ---TG--------------CC---AGG------------------------------------
DRw10         -------------------GT---T-T-A---------------------------------G-
DR1a-c       ---TG--------------CT---T--------------------------------------G-
DR cons       CACGTTTCTTGGAGCAGx xTAAGTCTGAGTGTCATTTCTTCAATGGGACGGAGCGGGTGCGGTTCCT
          10                 20                30                  40             50            60

30  D   R   Y   F   H   N   Q   E   Y   V   R   F   D   V  40 G   E   Y   R   A
DR cons       GGACAGATACTTCCATAACCAGGAGTACGTGCGCTTCGACAGCGTGGGGGAGTACCGGGCG
DRw52a        ---G----------------------------T-C-------------------------
DRw52b.1      ---G--------------C--------------C--------------------C-----
DRw52b.2      ---G--------------C--------------C--------------------------
DRw52b.3      ---G--------------C--------------C--------------------------
DRw52c        ---G---------------------------T------------------------T---
Drw12a,b      ---G--------------C-------------CT-C------------------------
                              30                          40
```

TABLE 1-continued

| | 50 V | T | E | L | G | R | P | D | A | E | Y | W | N | S | Q | K | D | L | L | E | Q | K |
|---|---|---|---|---|---|---|---|---|---|---|---|---|---|---|---|---|---|---|---|---|---|---|
| DR cons | GT GACGGAGCTGGGGGCGGCCTGATGCCGAGTACTGGAACAGCCAGAAGGACCTCCTGGAGCAGAA | | | | | | | | | | | | | | | | | | | | | |
| | 70 | | | | | 80 | | | | | 90 | | | | | 100 | | | | | 110 | |
| DR3a | ------------------------------------------------------------------ |
| DR3b | -------G---------------------------A----------------------------- |
| DR5a,b,c,e | ---------------------------T-------A----------------------------- |
| DR5d | ---------------------------T-------A----------------------------- |
| NEW | -------G-------------------------------------------------------T- |
| DRw6a | -----------------------------------A----------------------------- |
| DRw6c | -----------------------------------A---T------------------------- |
| DRw6b | -------G---------------------------A----------------------------- |
| DRw6d | -------G---------------------------------------------------------- |
| DRw6e | -----------------------T----------A----------------------------- |
| DRw8a&b | ------------------------T----------A----------------------------- |
| DRw8c | ------------------------T----------A----------------------------- |
| DRw8d | --------------------------T--------A----------------------------- |
| DRw53a | ------------AT---------A--T--------C-----A--A---T--C------------- |
| DRw53b | ------------AT---------A--T--------------A--A---T--C------------- |
| DRw53c | ------------AT---------A--T--------------A--A---T--C------------- |
| DRw4a-e | -------------------------T--C-----A----------------------------- |
| DR4f | -------------------------T--C-----A----------------------------- |
| DR7 | ---------A---CT--------T-----T-----A----------------------------- |
| DRw9 | ---------C-----GG-A----T-----------A----------------------------- |
| DR2a B3 | ---------C------G-A----T-----------A--G--T---------------------- |
| DR2b B3 | ---------C-----GG-A----T-----------A----------------------------- |
| DR2c B3 | ---------C-----GG-A----T-----------A----------------------------- |
| DR2a B1 | ----------------T--------T---------C----------------------T----- |
| DR2b B1 | ----------------T--------T---------C----------------------T----- |
| DR2c B1 | ----------------T--------T---------C----------------------T----- |
| DRw10 | ---------A----CG-G-----T-----------A-----C------------------C--- |
| DRw1a-c | ---------A----G-A------T-----------A-----C----------------------- |
| DR cons | GGACAGATACTTCCATAACCAGGAGAGTACGTGCGCTTCGACAGCGACGTGGGGGAGTACCGGGCG |
| | 70 | | | 80 | | | 90 | | | 100 | | | 110 | | | 120 | | | 130 | | |

| | 60 W | N | S | Q | K | D | L | L | E | Q | 70 K |
|---|---|---|---|---|---|---|---|---|---|---|---|
| DR cons | | | | | | | | | | | |
| DRw52a | -------G---------------------C----------- |
| DRw52b.1 | -------G--------------------------------- |
| DRw52b.2 | -------G--------------------------------- |
| DRw52b.3 | -------G--------------------------------- |
| DRw52c | ------------AG---------TC--C------------- |
| DRw12a | ------------AG---------TC--C---------A--- |
| DRw12b | ------------AG---------TC--C---T--------- |
| DR3a | ------------AG--------------------------- |
| DR3b | ------------AG-----------------A--------- |
| DR5a | ------------AG-----------------T----AG-C-G |
| DR5b | ------------AG-----------------A----AG-CG- |
| DR5c | ------------AG-----------------T----AG-CG- |
| DR5d | ------------AG-----------------T----AG-CG- |
| DR5e | ------------AG-----------------T----AG-C-G |
| NEW 1 | ------------AG-----------------A----AG-CG- |
| DRw6a | -------------------------------A----AG-CG- |
| DRw6c | -------------------------------A----AG-CG- |

TABLE 1-continued

|  |  |  |  |  |  |  |  |  |
|---|---|---|---|---|---|---|---|---|
| DRw6b | --- | --- | --- | --C- | --- | --G- | --C- | --- | G--G |
| DRw6a | --- | --- | --- | --- | --- | --- | --- | --- | --G |
| DRw6e | --- | --- | --- | AGC- | --- | --- | --A- | --- | AG-C- |
| DRw8a | --- | --- | --- | AGC- | --- | --- | --T- | --- | AG-C-G |
| DRw8b | --- | --- | --- | --- | --- | --C- | --A- | --- | AG-C-G |
| DRw8d | --- | --- | --- | --- | --- | --C- | --- | --- | --G |
| DRw53a | --- | --- | --- | --- | --C-T- | --G- | --- | --- | --G |
| DRw53b | --- | --- | --- | --- | --C-T- | --- | --- | --- | --G |
| DRw53c | --- | --- | --- | --- | --C- | --- | --- | --- | --G |
| DR4a | --- | --- | --- | --- | --- | --- | --- | --- | --G |
| DR4b | --- | --- | --- | --- | --- | --- | --A- | --- | AG-CG- |
| DR4d | --- | --- | --- | --- | --- | --- | --- | --- | --G |
| DR4c&f | --- | --- | --- | --- | --- | --- | --- | --- | --G |
| DR4e | --- | --- | --A- | AGC- | --- | --- | --A- | --- | --G |
| DR 7 | --- | --- | --- | TC-- | --C- | --- | --T- | --- | G-CG |
| DRw9 | --- | --- | --- | T-- | --C-T- | --- | --- | --- | --G |
| DR2a B3 | --- | --- | --- | --- | --C-T- | --- | --T- | --- | AG-C-G |
| DR2b B3 | --- | --- | --- | --- | --C-T- | --- | --T- | --- | AG-C-G |
| DR2c B3 | --- | --- | --- | --- | --C-T- | --- | --A- | --- | --GC |
| DR2d B1 | --- | --- | --- | --- | --C-T- | --- | --T- | --- | AG-C-G |
| DRw10 | --- | --- | --- | --- | --C-T- | --- | --T- | --- | --G |
| DRw1a | --- | --- | --- | --- | --- | --- | --- | --- | --G |
| DRw1b | --- | --- | --- | --- | --- | --- | --- | --- | AG-CG- |
| DRw1c | --- | --- | --- | --- | --- | --- | --A- | --- | AG-CG- |
| DR cons | GTGACGGAGCTGGGGCGGGGCCTGATGCCGAGTACTGGAACAGCCAGAAGGACCTCCTGGAGCAGAA |  |  |  |  |  |  |  |
|  | 140 | 150 | 160 | 170 | 180 | 190 |  |  |  |

|  |  |  |  |  |  |  |  |  |  |
|---|---|---|---|---|---|---|---|---|---|
|  | R | A | X | V | D | T | Y | C | R | H | N | Y | G | V | V | E | S | F | T | V | Q | R | R |
| DR cons | GCGGGGCCGxGGTGGACACCTACTGCAGACACAACTACGGGGTTGTGGAGAGCTTCACAGTGCAGCGGCGA |
| DRw52a | --- | --G-CG | --- | --- | --- | --- | --- | --- |
| DRw52b.1 | --- | --G-CA | --AT- | --- | --- | --- | --- | --- |
| DRw52b.2 | --- | --G-CA | --AT- | --- | --GT- | --- | --- | --- |
| DRw52b.3 | --- | --G-CA | --AT- | --- | --GT- | --- | --- | --- |
| DRw52c | --- | --G-CA | --AT- | --- | --GT- | --- | --- | --- |
| DRw12a | --- | --C-- | --- | --T-- | --C-- | --- | --- | --- |
| DRw12b | --- | --C-- | --- | --T-- | --C-- | --- | --- | --- |
| DR3a | --- | --G-CG | --A-- | --- | --- | --- | --- | --- |
| DR3b | --- | --G-CG | --A-- | --- | --GT- | --- | --- | --- |
| DR5a | --- | --C-- | --- | --- | --- | --- | --- | --- |
| DR5b | --- | --C-- | --- | --- | --- | --- | --- | --- |
| DR5c | --- | --C-- | --- | --- | --GT- | --- | --- | --- |
| DR5d | --- | --C-- | --- | --- | --- | --- | --- | --- |
| DR5e | --- | --CT- | --- | --- | --GT- | --- | --- | --- |
| NEW 1 | --- | --C-- | --- | --- | --- | --- | --- | --- |
| DRw6a | --- | --C-- | --- | --- | --GT- | --- | --- | --- |
| DRw6c | --- | --- | --- | --T-- | --- | --- | --- | --- |
| DRw6b | --- | --C-- | --- | --- | --GT- | --- | --- | --- |
| DRw6d | --- | --A-- | --- | --- | --- | --- | --- | --- |
| DRw6c | --- | --C-- | --- | --- | --- | --- | --- | --- |
|  | 80 | 90 |  |  |  |  |  |  |  |

TABLE 1-continued

| | 200 | 210 | 220 | 230 | 240 | 250 | 260 |
|---|---|---|---|---|---|---|---|
| DRw8a | ---- | --CT-- | ------ | ------ | ------ | ---GT- | ------ |
| DRw8b | ---- | --CT-- | ------ | ------ | ------ | ---GT- | ------ |
| DRw8c | ---- | --CT-- | ------ | ------ | ------ | ---GT- | ------ |
| DRw8d | ---- | ---A-- | ---T-- | ------ | ------ | ------ | ------ |
| DRw53a | ---- | ---A-- | ---T-- | ------ | ------ | ------ | ------ |
| DRw53b | --C- | ---C-- | ---T-- | ------ | ------ | ------ | ------ |
| DRw53c | ---- | ---A-- | ---T-- | ------ | ------ | ---GT- | ------ |
| DR4a | ---- | ---C-- | ------ | ------ | ------ | ------ | ------ |
| DR4b | ---- | ---C-- | ------ | ------ | ------ | ------ | ------ |
| DR4d | ---- | ---C-- | ------ | ------ | ------ | ------ | ------ |
| DR4c&f | ---- | ---A-- | ------ | ------ | ------ | ---GT- | ------ |
| DR4e | ---- | ---C-- | ------ | ------ | ------ | ---GT- | ------ |
| DR 7 | ---- | -G-CA- | GT G-- | ------ | ------ | ---GT- | ------ |
| DRw9 | ---- | ---A-- | GT G-- | ------ | ------ | ---GT- | ---A-- |
| DR2a B3 | --C- | ---C-- | ------ | ------ | ------ | ---GT- | ------ |
| DR2b B3 | --C- | ---C-- | ------ | ------ | ---C-- | ---GT- | ------ |
| DR2c B3 | ---- | ---C-- | ------ | ------ | ------ | ------ | ------ |
| DR2a B1 | ---- | ---C-- | ------ | ------ | ------ | ---GT- | ---T-- |
| DR2b B1 | --C- | ---C-- | ------ | ------ | ------ | ---GT- | ------ |
| DR2c B1 | --C- | ---C-- | ------ | ------ | ------ | ---GT- | ------ |
| DR2d B1 | ---- | ---T-- | ------ | ---T-- | ---C-- | ---GT- | ------ |
| DRw10 | ---- | ---C-- | ------ | ------ | ------ | ---GT- | ------ |
| DR1a | ---- | ---C-- | ------ | ------ | ------ | ---GT- | ------ |
| DR1B | ---- | ---C-- | ------ | ------ | ------ | ---GT- | ------ |
| DR1c | ---- | ---C-- | ------ | ------ | ------ | ---GT- | ------ |
| DR cons | GCGGGCCGxG | GTGGACACCT | ACTGCAGACA | CAACTACGGG | GTTGTGGAGA | GCTTCACAGT | GCAGCGGCGA |

TABLE 2

| Associated HLA Typing | 6 10 20 30 40 50 60 70 80 90 |
|---|---|
| cons. | RFLE--KS ECHFFNGTER VRFLDRYFHN QEEYVRFDS DVGEYRAVTE LGRPDAEYWNS QKDLLEQRRAA VDTYCRHNYG VVESTVQRR |
| DR3a/Dw3 | (---) RFLE- -- Y------- --------N- --------- --------- --------- --------- K- GR- N- --- |
| DR3b/Dw | (---) ----- YST- --E------ --------N- --------- --------- --------- --------- K- GR- N- -G- |
| DRw6a/Dw18 | (---) ----- YST- --------- --------N- --F------ --------- --------- -----I -DE- --------- -G- |
| DRw6c/Dw19 | (---) ----- YST- --------- --------N- --F------ --------- --------- -----I -DE- --------- -G- |
| DR6eJ | (---) ----- YST- --------- -------Y-- -F------- --------- --------- -----I -DK- --------- -G- |
| DR6fJ | (---) ----- YST- --------- -------Y-- --------- --------- --------- -----I -DE- --------- -G- |
| DRw8a/Dw8.1 | (---) ----- YSTG- -Y- --------- -------Y-- --------- ----S---- --------- ---F- -D- -L- --------- -G |
| DRw8b/Dw8.2 | (---) ----- YSTG- -Y- --------- -------Y-- --------- ----S---- --------- ---F- -D- -L- --------- -G- |
| DRw8c/Dw8.3 | (---) ----- YSTG- -Y- --------- -------Y-- --------- ----S---- --------- -----I- -D- -L- --------- -G- |
| NEW 1 | (---) ----- YST- --------- -------Y-- --------- ----S---- --------- -----I- -D- -L- --------- -G- |
| NEW 2 | (---) ----- YSTG- --- --E------ --------F- --------- --------- --A- H--- ----R- -E- --------- --- |
| DR5a/Dw5a S | (---) ----- YST- --------- --------N- -F------- --------- --------- ---F- -D- --------- -G- |
| DR5b/Dw5b M | (---) ----- YSTG- --- --E- H--- --------LL -F------- --------- ----E---- -----I- -DE- --------- --- |
| DR5c/Dw5c E | (---) ----- YSTG- --- --E- H--- --------LL -F------- --------- ----E---- -----I- -DE- --------- --- |
| DRw6b/Dw9 | (---) ----- YST- --------- --------F- --------- --------- --A- H--- ----R- -E- --------- --- |
| DRw6d/Dw9 | (---) ----- YST- --------- -------YH- --------- --------- --------- --------- --------- -G- |
| DRw12a | (---) ----- YSTG- -Y- --------- -------YH- --------- --------- ---V- -S- --------I- -D- --------- -A- |
| DRw12b | (---) ----- YSTG- -Y- --------- -------YH- --------- --------- ---V- -S- ---F- -D- --------- -A- |
| DR4a/Dw4 | (---) ----- QV- H- --------- -------YH- --------- --------- --------- -----I- -DE- --------- --- |
| DR4b/Dw10 | (---) ----- QV- H- --------- -------YH- --------- --------- --------- --------K- --------- --- |
| DR4c/Dw13 | (---) ----- QV- H- --------- -------YH- --------- --------- --------- -----I- -DE- --------- --- |
| DR4d/Dw14 | (---) ----- QV- H- --------- -------YH- --------- ----S---- --------- --------E- --------- --- |
| DR4e/Dw15 | (---) ----- QV- H- --------- -------YH- --------- --------- --------- --------- --------- --- |
| DR4f/KT2 | (---) ----- QV- H- --------- -------YH- --------- --------- --------- --------E- --------- --- |
| DR4g/Dw13.2 | (---) ----- QV- H- --------- -------YH- --------- ----S---- --------- --------E- --------- -G- |
| DR4h/Dw14.2 | (---) ----- QV- H- --------- -------YH- --------- --------- --------- ---F- -D- --------- -G- |
| DR7/Dw7 | (---) ----- WQG- YK- Q- E- L- Y- --------- -F------- --------- ---V- -S- --------I- -D- -GQ- --V- -G- |
| DR9/ | (---) ----- KQD- F- Y. H- GI Y- --------N- --------- --------- ---V- -S- ---F- -R- -E- -V- -A- |
| DR2a/w2 | (---) ----- WQP- R- --------- --------Y- --------- --------- --------- -----I- -A- --------- -G- |
| DR2b/w12 | (---) ----- WQP- R- --------- --E- H--- ---S----- --------- --------- -----I- -A- --------- -G- |
| DR2c/w21 | (---) ----- WQP- R- --------- --E- H--- ---S----- ------R-- --------- --------- --------- -G- |
| DR2d/w22 | (---) ----- WQP- R- --------- --E- H--- ---S----- ------R-- --------- ---F- -D- --------- -G- |
| DR1a/w1 | (---) ----- WQL- F- --------- --------Y- -F------- --------- --------- --------- --------- -G- |
| DR1b/w20 | (---) ----- WQL- F- --------- --------- -A. Y---- --------- --------- -----I -DE- --------- -A- |
| DR1c/wB0N | (---) ----- WQL- F- --------- --------- ---FL---- --------- --------- ----R- --------- --------- --- |
| DRw10 | (---) ----- EV- F- --------- --------- --------- --------- --------- --------- --------- --- |
| DR B alleles at locus B3/B4 | |
| DRw52a/w24 | (---) ----- LR- --------- -------A- --------- --------- --------- --------- K- GR- N- --- |
| DRw52b1/w25 | (---) ----- LL- --------- --E- H--- -A--Y---- --------- --------- --------- K- GQ- N- --- |
| DRw52b2 | (---) ----- LL- --------- --E- H--- -A------- -----R---- --------- --------- K- GQ- N- --- |
| DRw52b3 | (---) ----- LL- --------- --E------ -A------- -----R---- --------- --------- K- GQ- N- --- |
| DRw52c | (---) ----- LL- --------- --E------ -F--F---- --------- --------- --------- K- GQ- N- --- |
| DRw53 | (---) ----- QA- C- -L- WN- I- -I Y- -A- YN- -L- -Q- --------- --------- --------- -R- -E- --------Y- -A- |
| DRw53.2 | (---) ----- QA- C- -L- -N- I- -I Y- -YN- -L- -Q- --------- --------- --------- -R- -E- --------Y- --- |
| DR2a/w2 | (---) ----- QQD- Y- --------- H- DI Y- --------- --------- --------- ---F- -D- --------- -G- |
| DR2b/w12 | (c---) ----- QQD- Y- --------- H- GI Y- -DL------ --------- --------- ---F- -D- --------- -G- |
| DR2c/w21,22 | (c---) ----- QQD- Y- --------- H- GI Y- -N------- --------- --------- -----I- -A- --------) |

TABLE 2-continued

| cons | RFLE- - KS ECHFFNGTER VRFL DRYFHNQEEY VRFDS DVGEYRAVTELGRP DAEYWNS QKDLLEQRRAAVDTYCRHNYGVVES FTVQRR |

Serological and cellular specificities assigned to the cell from which sequences were derived are indicated. When multiple alleles are associated with a single serological specificity, individual alleles are differentiated by arbitrary assignment of letters.

Of the HLA-DR beta sequences given in Table 1, DRw8b, DRw8c, DRNew 1 and 2, DRw12 and DR1c are new sequences identified as part of the present invention. The consensus sequence is set forth along the top of each table. The various alleles have the same sequence as the consensus sequence at all positions noted with a dash (-), and differ from the consensus sequence where a nucleotide (A,G,C or T) is given. As the table illustrates, there is substantial polymorphism among the HLA-DR sequences shown, all of which have been identified in the population. Some of these sequences are closely similar, and vary by as little as a single nucleotide. The need for a typing method which can identify single nucleotide differences at single locations is apparent, although it should not be necessary to detect silent changes, i.e., mismatches which do not change the resulting amino acid.

HLA-DR typing is particularly difficult because of the large number of sequences known to exist in the general population. For this purpose, a set of oligonucleotide probes according to the invention has been developed for discerning among DR sequences. Table 3 sets forth the sequences of preferred probes according to the invention, Table 4 describes the probes used to identify groups of alleles approximating the serologically defined specificities, and Table 5 describes the combinations of probes used to identify individual HLA-DR alleles. In Tables 3 and 4, the protein sequences encoded by oligonucleotide probes are indicated by the single letter amino acid code followed by the position of the first residue.

TABLE 3

| PROBE SEQUENCE | NAME | AMINO ACIDS |
|---|---|---|
| G GAA AGA TGC AT | ECI28 | ERCI28 |
| GAG CAG GCG CGG | QA70 | EQAR69 |
| GAC AAC TAC TGC | N77.1 | DNYC76 |
| TC TAT CAC CAA GA | H33 | FYHQE31 |
| CCT GAT GAG GAG | E58 | PDEE56 |
| T GCT GCG GAG CA | A57 | AAEH57 |
| AG GAG GAG AAC G | N37 | QEEN34 |
| GAA AGA CTC TTC T | E28L30 | ERLF28 |
| AGG CGG GCC CTG | L74 | RPAL71 |
| CGG TAT CTG CAC | YLH26 | RYLH25 |
| G GAA AGA CGC GT | ERV28 | ERRV28 |
| G GAG CTC CTG CG | LL37 | ELLR36 |
| G GAC AAT TAC TGC | N77.2 | DNYC76 |
| GG AAC CTG ATC A | N26I28 | RNLI25 |
| GG AAC AGC CAG A | Cons. 61 | WNSQ61 |
| AC TTC TAT AAC CAG GAG GA | Y32 | YFYNQEE30 |
| G GTT GTG GAG AG | V86 | VVES85 |
| G GTT GGT GAG AG | G86 | VGES85 |
| AAG GAC TTC CTG | F67 | KDFL65 |
| AAG GAC CTC CTG | KL65 | KDLL65 |
| A GAG GAG GAC TT | DL37 | EEDL35 |
| AC TAC GGG GCT GTG GAG AG | A85 | NYGAVES82 |
| TG CAC AGA GGC ATC TAT AA | H28 | LHRGIYN27 |
| CTG GAA GAC AGG CGC GCC G | DR70.1 | LEDRRA68 |
| AG AAG CGG GCC GCG | K71 | QKRAA70 |
| GAA GAC GAG CGG | DE70.1 | EDER69 |
| CAG AGG CGG GCC GAG G | R71E74 | QRRAE70 |
| AG AGG CGG GCC GCG | R71A74 | QRRAA70 |
| AC CAA GAG GAG TCC | S37 | NQEES33 |
| CTG GAG AGA TAC | E28 | LERY27 |
| G GAG TTC GTG CG | F37 | EFVR36 |
| CTG GAA GAC AAG | D70 | LEDK68 |
| G GAG TTC CTG CG | FL37 | EFLR36 |
| TC CTG GAG AGA CA | H30 | FLERH26 |
| AC AGG CGG GCC GCG | R71 | QRRAA70 |
| C TTC CTG GAA GAC GA | F67DE70 | FLEDE67 |
| AC ATC CTG GAA GAC G | I67D70 | DILED66 |
| CAA GAG GAG AAC | N37.1 | QEEN34 |
| G GAC ATC CTG GAA GAC AGG | IDR67 | DILEDR66 |
| G GAC TTC CTG GAA GAC AGG | FDR67 | DFLEDR66 |
| G CGG CCT AGC GCC GAG TAC | S57 | RPSAEY55 |
| C AGG CGG GGC CA | GQ73 | RRGQ71 |
| GAC AGG CGC GCC | DR70.2 | DRRA68 |
| C GGG GTT GGT GAG AGC TTC | VAL86 | GVVESF84 |
| C GGG GTT GTG GAG AGC TTC | GLY86 | GVTESF84 |
| CAA GAG GAG TCC GT | S37.1 | QEESV34 |
| AA GAG GAG TCC G | S37.2 | QEES34 |
| AC TTC CTG GAA GAC G | F67D7071 | DFLED66 |
| C ATC CTG GAA GAC GA | I67DE70 | ILEDE67 |
| CCT AGC GCC GAG | S57.1 | PSAE56 |
| G CCT AGC GCC GAG T | S57.2 | PSAE56 |
| AC TCT ACG TCT G | ST11 | QSTS11 |
| TAC TCT ACG GGT | YSTG10 | YSTG10 |
| CAG GCT AAG TGT | A11 | QAKS10 |

TABLE 3-continued

| PROBE SEQUENCE | NAME | AMINO ACIDS |
|---|---|---|
| CTG TGG CAG GGT | W9G11 | LWQG8 |
| TTG TGG CAG CTT | W9L11 | LWQL8 |
| G GAG GTT AAG TT | EV10 | EVKF10 |
| G CCT AAG AGG GA | P11RI3 | PKRE11 |
| G GAG GTT AAA CAT | VKH11 | QVKH10 |
| GAG CTG CTT AAG | LL10 | ELLK9 |
| CAG CTG CGT AAG | LR10 | ELRK9 |
| TG CAG CAG GAT A | Q9D11 | LQQD9 |
| TG AAG CAG GAT A | K9D11 | LKQD9 |
| CTG GAA GAC GAG CGG GCC G | DE70.2 | LEDERA68 |
| C TTC CTG GAA GAC AG | F67DR70 | FLEDR67 |

TABLE 4

| PROBE SEQUENCE | NAME | AMINO ACIDS | ASSOCIATED SEROLOGICAL SPECIFICITY |
|---|---|---|---|
| G GAA AGA TGC AT | ECI28 | ERCI28 | DR1 |
| GAG CAG GCG CGG | QA70 | EQAR69 | DR2 |
| GAC AAC TAC TGC | N77.1 | DNYC76 | DR3 |
| TC TAT CAC CAA GA | H33 | FYHQE31 | DR4 |
| CCT GAT GAG GAG | E58 | PDEE56 | DR5 |
| T GCT GCG GAG CA | A57 | AAEH57 | DRw6b, NEW 2 |
| AG GAG GAG AAC G | N37 | QEEN34 | DR3, DRw6a, c, d, NEW 1 |
| G CGG CCT AGC GCC GAG TAC | S57 | RPSAEY55 | DRw6e, 6f, DRw8a, 8c, DR4e |
| GAA AGA CTC TTC T | E28L30 | ERLF28 | DR7 |
| AGG CGG GCC CTG | L74 | RRAL71 | DRw8 |
| CGG TAT CTG CAC | YLH26 | RYLH25 | DR9 |
| G GAA AGA CGC GT | ERV28 | ERRV28 | DRw10 |
| G GAG CTC CTG CG | LL37 | ELLR36 | DRw12 |
| G GAC AAT TAC TGC | N77.2 | DNYC76 | DRw52 |
| GG AAC CTG ATC A | N26I28 | RNLI25 | DRw53 |
| GG AAC AGC CAG A | Cons. 61 | WNSQ61 | HLA-DR |

TABLE 5

| ALLELE | PROBES | SER. | CELLULAR |
|---|---|---|---|
| DR1a | W9L11, ECI28, S37, R71A74, KL65, G86 | DR1 | Dw1 |
| DR1b | W9L11, ECI28, S37, R71A74, KL65, A85 | DR1 | Dw20 |
| DR1c | W9L11, ECI28, S37, DE70.1, G86, KL65, I67D70 | BR | BON |
| DR2: | | | |
| a | β1 P11R13, QA70, Y32, V86 β3 Q9D11, DL37, DR70.1, G86, F67, F67D70, FDR67 | DR2(w15) | Dw2 |
| b | β1 P11R13, QA70, Y32, G86 β3 Q9D11, DR70.1, H28, G86, F67, F67D70, FDR67, N37.1 | DR2(w15) | Dw12 |
| c | β1 P11R13, DR70.1, Y32, G86, F67, F67D70, FDR67, N37.1 β3 Q9D11, QA70, H28, A85 | DR2(w16) | Dw21 |
| d | β1 P11R13, DR70.1, KL65, Y32, G86 β3 Q9D11, QA70, H28, A85, N37.1 | DR2(w16) | Dw22 |
| DR3: | | | |
| a | ST11, R74N77, N37, KL65, V86, N77.1 | DR3(w17) | Dw3 |
| b | ST11, R74N77, N37, K65, E28, G86, N77.1 | DR3(w18) | NEW |
| DR4: | | | |
| a | VKH11, H33, K71, G86, KL65 | DR4 | Dw4 |
| b | VKH11, H33, DE70.1, I67D70.1, V86 | DR4 | Dw10 |
| c | VKH11, H33, R71E74, V86 KL65 | DR4 | Dw12 |
| d | VKH11, H33, R71A74, V86 KL6 5 | DR4 | Dw14 |
| e | VKH11, H33, S57, R71A74, G86, K65 | DR4 | Dw15 |
| f | VKH11, H33, R71E74, S37, V86, KL65 | DR4 | |
| g | VKH11, H33, R71E74, G86, KL65 | DR4 | |
| h | VKH11, H33, R71A74, G86 KL65 | DR4 | |
| DR5: | | | |
| a | ST11, E58, R71, G86, FDR67, F67, F67DR70 | DR5 (w11) | |
| b | ST11, E58, I67D70, V86, DE70.1 | DR5 (w11) | |
| c | ST11, E58, F67DE70, V86, DE70.1, F67 | DR5 (w11) | |
| d | ST11, E58, F67DE70, N37.1, V86, DE70.1, F67 | DR5 (w11) | |
| e | ST11, E58, R71, V86 F67, FDR67, F67DR70 | DR5 (w11) | |
| DR6: | | | |
| a | ST11, N37, DE70.1, I67D70; V86 | DRw6 (w13) | Dw18 |
| b | ST11, A57, F37, V86 KL65 | DRw6 (w14) | Dw9 |
| c | ST11, N37, DE70.1, I67D70, G86 | DRw6 (w13) | Dw19 |
| d | ST11, N37, R71A74, G86 E28, KL65 | DRw6 (w14) | Dw16 |
| e | ST11, D70, S57, G86 | DRw6 | |
| f | ST11, DE70.1, I67D70, S57, V86 | DRw6 | |
| DR7: | W8G11, E28L30, F37, G86 | DR7 | Dw7 |
| DR8: | | | |
| a | YSTG10, L74, S57, FDR67, G86, F67DR70, F67 | DRw8 | DWA |

TABLE 5-continued

| ALLELE | PROBES | SER. | CELLULAR |
|---|---|---|---|
| b | YSTG10, L74, FDR67, G86, F67DR70, F67 | | |
| c | YSTG10, L74, S57, IDR67, G86 | | |
| DR9: | K9D11, YLH26, H28, N37.1, F67, G86 | DR9 | |
| DR10: | EV10, ERV28, RR70, ARY38, KL65, G86 | DRw10 | |
| DR12: | | | |
| a | YSTG10, LL37; IDR67; DR70.1; A86 | | |
| b | YSTG10, LL37; FDR67; DR70.1, F67, F67DR70, A86 | | |
| DRw52: | | | |
| a | LR11, N77.2; FL37, G86 | DRw52 | Dw24 |
| b | LL10, N77.2; H30; V86, G86 | | Dw25 |
| c | LL10, N77.2; F37, E28; V86 | | Dw26 |
| DRw53: | | | |
| a | A11, N26I28, KL65, V86 | DRw53 | |
| b | A11, N26I28, KL65, V86 | | |
| c | A11, N26I28, KL65, V86 | | |
| NEW: | | | |
| 1 | ST11, E28, N37, KL65, L74, G86 | | |
| 2 | YSTG10, F37, A57, KL65, V86 | | |

The probes listed in Table 4 can be used to group alleles according to serological specificity (i.e., one or more general DR types, such as DR1). To determine which of the HLA-DR1 a, b, or c alleles is present, further hybridizations must be carried out using other probes which selectively hybridize at the locations at which the a, b and c alleles differ. The sequences of preferred probes used to carry out these successive hybridizations are set forth in Table 3, and the probe combinations used to identify each HLA-DR allele are given in Table 5. Thus, HLA-DR typing according to the invention is preferably carried out in two stages, one to determine which of the serological groups the sample belongs to using a probe specific for that group, and a second stage using additional probes to determine which specific allele within that group is present. As Table 5 illustrates, virtually all HLA-DR alleles must be identified by a combination (2 or more) probes.

Not all potential probe sequences prove useful in practice, for reasons that include, but are not limited to:

(a) inability to resolve single base pair mismatches due to facts such as purine content, nature or position of potential mismatches;

(b) formation of secondary structures;

(c) hybridization to multiple alleles (these probes are useful if specificity is determined by SSA); and (d) multiple hybridization sites.

However, it is generally possible to design a probe sufficiently long to hybridize selectively with the desired HLA-DR sequence if the sequence is present an a test sample, but not so long that the probe hybridizes in spite of a single base pair mismatch. For this purpose, oligonucleotides ranging from 12 to 25, particularly 12 to 20 nucleic acids in length have proven most successful.

The exact length of the probe is not critical so long as the probe is within the appropriate size range and includes the characterizing (variant) part(s) of the sequence to be detected. Thus, for example, the DR3a,b probe set forth above is one of a family of probes of the formula:

$$5'-(L)-A-(R)$$

wherein L is a sequence of from 0 to 24 nucleotides to the left of adenosine position 217 for DR3a or DR3b, and R is a sequence of from 0 to 24 nucleotides to the right of the adenosine unit at position 217, provided that the total length of the sequence is 25 or less (e.g., if R is a sequence of 24, then L is a sequence of 0, and the like.) Similar definitions apply for the other probe sequences described above by obtaining the formulas for R and L from the sequences shown in Table 1 at the positions at either end of the nucleotide or sequence of nucleotides that varies from the consensus sequence.

The probes listed in Table 3 are less than 25 nucleotides long and could be lengthened at either end to include up to 13 additional adjoining nucleotides from the sequence of the HLA-DR beta allele associated with each probe. For example, the DR3a,b probe set forth above is one of a family of probes of the formula:

$$5'-(R')GGACAACTACTG(L')$$

wherein R' is a sequence of from 0 to 12 rightmost nucleotides of the sequence GCGGGGCCxGGT, wherein x is A or G, and L' is a sequence of from 0 to 12 leftmost nucleotides of the sequence CAGACACAACTA, provided that the sum of nucleotides of R' and L' is about 13 or less. Since longer oligonucleotides are more difficult to use, the sum of R' and L' is preferably 8 or less. It should further be understood that each probe could also be the complement of the sequences given above.

The oligonucleotide probes according to the invention further comprise a labelling substance which allows a successful hybridization to be detected after excess unbound probe (i.e., probe that is not complementary to the target sequence) has been removed, e.g., washed away. Radioactive isotopes such as $^{32}p$ can be readily incorporated as part of the probe. A non-radioactive detection system, e.g., an enzyme-based assay using digoxigenin or biotin as the labelling substance, is most preferred. However, other types of labelling substances can also be employed. Numerous methods for preparing labelled oligonucleotide probes are well known.

The proper selection of primers is essential to the amplification step if the polymerase chain reaction (PCR) method is to be used. For purposes of amplification of all products at a given locus, the primers must hybridize to sequences that bracket the region of interest. Primers must hybridize with sufficient specificity to limit amplification (logarithmic synthesis) to the desired targets, and must hybridize with all desired alleles (e.g., all HLA-DR alleles for purposes of comprehensive HLA-DR typing). The effectiveness of primers is a function of the sequence of the primers as well as the reaction conditions for the polymerase chain reaction, e.g., temperature of annealing, time of annealing, temperature of denaturation, time of denaturation, and salt concentration.

It has been found according to the invention that primers consisting essentially of the sequences below can be successfully used to carry out amplification:

| DR BETA (16–23) | 5'-ATTTCTTCAATGGGACGGAGC |
| DR BETA (87–94) | 5'-CGCCGCTGCACTGTGAAGCTCTC |

The first sequence corresponds to the DR beta sequence at the position indicated in Table 1, and the second sequence is the complement of the sequence given in Table 1, in reverse order. Probes of these sequences have proven highly successful in amplifying DNA from the HLA-DR beta locus. Although some polymorphism occurs at DR beta positions 16–23 and 87–94, all known HLA-DR alleles can be amplified using these primers under a wide variety of conditions.

Since effective PCR primers usually range between 15–30 nucleotides, it will be appreciated that other effective primers partially including or overlapping the foregoing sequences could be designed. Thus, one generally effective set of PCR primers according to the invention may be defined as a pair of oligonucleotides having at least 12 nucleotides which correspond to the HLA-DR beta sequence, one of which will hybridize with the HLA-DR consensus sequence within positions 16 to 23 and the other of which will hybridize with the HLA-DR consensus sequence within positions 87 to 94, more generally at position 79 or beyond. Such primers allow amplification of HLA-DR beta DNA within the range from positions 24 to 86, wherein a major portion of DR polymorphism occurs.

A second generally effective set of PCR primers according to the invention may be defined as a pair of oligonucleotides having at least 12 nucleotides, one of which will hybridize with the HLA-DR consensus sequence within positions 5 to 8 and the other of which will hybridize within positions 87 to 94, more generally at positions 79 and beyond:

| DR BETA (Intron-8) | 5'GTCCCCACAGCACGTTTCTTG |
| DR BETA (87–94) | 5'CGCCGCTGCACTGTGAAGCTCTC. |

Such primers allow amplification of HLA-DR beta genes within the range from positions 9 to 86, allowing detection of polymorphism at locations 11 to 23 wherein additional HLA-DR polymorphism occurs.

While a number of specific probe sequences can be designed and used to detect a given variation from the consensus sequence at a specific location, it has been discovered that some such probes unexpectedly perform better than others in practice, and that the conditions (e.g., temperature, salt concentration, solvent) under which probe hybridization and washing is carried out have a strong influence on the result. Under some conditions, for example, a probe specifically designed to hybridize with a sequence characterizing a single DR allele might also hybridize with other, closely similar alleles. For this reason the invention provides a series of comprensive controls to avoid false positive results which can occur when this happens.

For example, at a particular region of an HLA locus, there may be multiple allelic sequences (e.g., 22 for the 67–74 region of HLA-DR). Some of these are very different from each other and are easily resolved by oligonucleotide probe hybridization (e.g., sequence from 5c,d and 52a). However, some alleles are very similar and much more difficult to resolve. An example of SSOPH in this region is detection of the alleles designated 5c and 5d which are distinguished from other alleles of the "5" grouping by the polymorphic residues located between positions 67 and 74. Assignment of these alleles requires probes that will differentiate this sequence (T-------AG-CG; Table 1) from all others.

A probe having the sequence 5'-TTCCTGGAAGACGA (for detecting T-------AG-CG-) was synthesized and conditions were determined to achieve sequence-specific hybridization with this probe (i.e., washing removed probe bound to all other sequences). However, when this was implemented for routine testing, additional hybridization with alleles designated 5b,6a,6c,4b, and 1c was occasionally observed. If the experiments had been performed with a single negative control that was less similar to the target sequence, such as the 5a,5e sequence, the lack of specificity of the hybridization would not have been detected. In this case, false positive hybridization with unknown samples containing 5b,6a,6c,4b, or 1c. Appropriate controls are required to confirm absolute specificity of hybridization.

Subtle differences can result in loss of specificity of a hybridization experiment. On many occasions, the inclusion of a comprehensive panel of controls (all possible allelic sequences) in carrying out the method of the invention has resulted in detection of the inadequate specificity of a particular hybridization. The inclusion of comprehensive controls can also detect certain errors by the technician, for example, accidental mixing of probes in a single hybridization. On many occasions, the inclusion of comprehensive controls allowed detection of assay failures that could not have been anticipated.

The HLA typing method of the invention has proven highly useful as part of a method for matching a potential tissue donors, particularly for bone marrow, with a patient receiving the transplant. In general, such a method involves performing some or all of HLA A, B, C, DQ, DP and DR typing on the potential donor and comparing the results to determine the extent of compatibility between the donor and recipient. Complete identity is not absolutely required to achieve a fully successful transplant. This method, which can be utilized with other types of human or animal tissue as well, is provided in the example below.

For the HLA-deficient SCID patient who was the subject of this example, serological HLA typing of freshly prepared cells failed to detect most HLA products. Mitogen/lymphokine treatment was unable to induce detectable levels of HLA-B, -DR, or -DQ products. However, analysis of the patient's DNA by SSOPH, which is not dependent upon protein expression, was possible. The combined utilization of serological and SSOPH analysis allowed detection of HLA-A2; B13; Cw4, w6; DR7, w11a, w52b, w53; DQw2, w7. B35 was not tested for, but was predicted by the haplotypes of family members.

SSOPH identifies relevant HLA polymorphism and detects single base pair differences that correspond to single amino acid differences in the proteins. In the example below, SSOPH distinguished between between three possible types of DRw11 alleles and three possible types of DRw52 alleles. This level of resolution was useful in donor selection because it confirmed that both donor and recipient shared the same subtypes, DRw11a and DRw52b. Matching with a higher degree of specificity results in less graft rejection and reduction in frequency and severity of graft-versus-host disease.

Detection of HLA polymorphism at the level of single amino acid differences provides the opportunity to establish a priority system for HLA matching in selection of optimal donors for transplants. By SSOPH analysis of bone marrow transplantation donor/recipient pairs, each polymorphism can be evaluated for its effect on the outcome of transplantation. In addition, each polymorphism can be correlated with the extent of serological and cellular alloreactivity. Finally, each polymorphism can be mapped onto the HLA structure. This information can be combined to generate a scale rating each position according to its functional importance. Allowable mismatches may be identified using this system, and use of this information should widen the range of potential donors for unrelated donor tissue transplants.

According to an alternative form of the invention, typing is again conducted in two stages. In the first stage, subject DNA from highly conserved regions is amplified and then hybridized with labelled probes to identify groups of alleles (groups usually organized according to association with a single serologically defined specificity such as DR1,2,3,4,5, w6,7,w8,9,w10,w12,w52,w53). The purpose of the first stage of testing is to establish the number of alleles present in each sample under conditions which substantially reduce the likelihood of false negative results due to failed amplification. Use of primers encoding fairly well conserved regions of a locus will increase the likelihood that unknown alleles will be amplified and potentially detected by hybridization with oligonucleotide probes. Furthermore, failure to produce an amplified product will indicate a failure of the assay.

In the second stage, the group identified in the first stage determines which of a set of allele-specific primers will be used for sequence-specific amplification (SSA) by means of the polymerase chain reaction process. The first of two primers for second stage amplification comprises a sequence common to each allele of the group identified in stage one (but different from other groups identified in stage one) optionally attached to a group such as biotin useful in subsequent selection, as described below.

The second primer is actually a mixture of different labelled primers, complementary to two or more sequences within the group. Each such primer comprises one of the foregoing sequences and a labelling substance which differentiates that primer from the other primers in the mixture, for example, a dye with distinguishable fluorescence.

Polymerase chain reaction (PCR) amplification is then performed using the first primer and a mixture of second primers that encode polymorphic sequences. DNA containing the first primer can be removed from the mixture by means of the selection agent. For example, biotin bound to the first primer allows it to be removed by pouring the mixture over streptavidin-coated beads, or free first polymer may be removed by gel electrophoresis. Both unincorporated primer and amplified DNA including the first primer become bound and are thereby removed from the mixture. The amplified DNA will include a dye-labelled second primer from the second primer mixture. Amplification conditions must be empirically determined to achieve desired specificity. Since amplification will take place for only dye-labelled primers represented in the target DNA, products only, product(s) corresponding to the second primer bind to the beads. As a result, the color of the beads indicates the presence of the specific polymorphic sequence present in the subject sample.

This method eliminates the need to use radiolabelled hybridization probes in the second stage, and its use could be expanded to cover first stage typing as well. Its advantages include simplicity and adaptability to automation. It provides a convenient way to characterize each allele by detecting polymorphic sequences at multiple positions in the molecule. For example, if the presence of a DRw8 allele was indicated by a stage 1 analysis, SSA could be used to test for sequences encoding polymorphic amino acids at positions 32, 57, 67/70, 74 and 86. SSA could be carried out in 5 separate tubes, each containing a cocktail of primers encoding polymorphic sequences associated with each position and 8/12-specific primer (5'-GTACTCTACGGGTGAGT-GTT).

It is possible to eliminate stage one of the foregoing procedure and use SSA to test for each allele directly. However, if SSA is performed by itself to detect the presence of a single allele or a group of alleles, it can be difficult to distinguish between a failed assay and absence of the allele. Thus, the foregoing two-stage method is preferred.

Sequence-specific hybridization to products of a locus-specific amplification is incapable of resolving certain combinations of alleles. For example, a combination of a 4 and 1 with positive hybridization for sequences encoding DE70, 71 and QRRAA70–74 cannot differentiate between 1c,4d or 1a,4b combinations. This problem can be resolved by sequence-specific amplification, eliminating the need to conduct several probe hybridizations as described above to identify a specific allele.

New alleles comprising different combinations of known polymorphic residues can be defined, and new alleles lacking a previously defined sequence can be detected by the lack of amplification at one or more positions. Further, this method can be used to carry out a comprehensive analysis of HLA polymorphism in as little as 0.5–2 days, the second stage of the process requiring only about 4 hours.

EXAMPLE

In the following procedures, oligonucleotides were synthesized by a Gene Assembler (Pharmacia, Piscataway, N.J.) using phosphoramidite chemistry. Oligonucleotides were purified using OPC cartridges (Applied Biosystems, Foster City, Calif.) or gel electrophoresis. Lymphoblastoid cell lines (LCL) used were distributed and characterized by the 10th International Histocompatibility Workshop.

A. Serological analysis

Heparin-treated venous blood from the subject was incubated with carbonyl iron, and peripheral blood lymphocytes (PBL) were obtained by centrifugation through Ficoll-Hypaque gradients (1,077 g/ml). Cells were washed, T- and B-cells were separated by nylon adherence, and HLA typing was performed by standard microlymphocytotoxicity assays, according to Danilovs, et al, *Joint report: B lymphocyte isolation by thrombin-nylonwool*, Histocompatibility Testing 1980, UCLA Press/Los Angeles, pp. 287–288, and van Rood, et al., 1975, *Tissue Antigens* 5:73–79. Serological specificities were assigned according to WHO nomenclature adopted following the 10th International Histocompatibility Workshop as described in Bodmer, et al., 1988, *Tissue Antigens* 32:177–187. DNA was isolated from blood cells by salting out as described in Miller, et. al., 1988, *Nuc. Acids Res.* 16:1215. Primer-directed enzymatic amplification of DNA was accomplished using the polymerase chain reaction as described in Saiki, et. al., 1988, *Science* 239:487–491. 100 µl reaction mixtures contained 1.0 to 3.0 µg genomic DNA, 200 µM each of deoxynucleoside 5'-triphosphate, 1 µM of each primer; 50 mM Tris-HCl, pH 8.3; 1.5 mM $MgCl_2$, and 0.01% (w/v) gelatin. Primers for amplification of segments of the HLA genes in the first domain exon are described in Table 6:

TABLE 6

| NAME | | SEQUENCE |
|---|---|---|
| DR BETA | (16–23) | 5'-ATTTCTTCAATGGGACGGAGC |
| DR BETA | (87–94) | 5'-CGCCGCTGCACTGTGAAGCTCTC |
| DQ BETA | (14–20) | 5'-TGTGCTACTTCACCAACGGG |
| DQ BETA | (83–89) | 5'-CGTGCGGAGCTCCAACTGGT |
| CLASS I | (1–6) | 5'-GCTCCCACTCCATGAGG |
| CLASS I | (85–91) | 5'-CGGCCTCGCTCTGGTTG |

The names of the primers include numbers which correspond to the location of the amino acid residues that are encoded by each primer.

Samples were boiled for 1 min, transferred to a 94° C. heat block, and 1–2 units of Taq polymerase (Perkin Elmer Cetus, Norwalk, Conn.) were added. The reactions consisted of 30–50 cycles of denaturation (94° C.), annealing for 1–2 min (35° C. for HLA-DQ; 55° C. for HLA-B and -DR), and polymerization (72°–74° C.) in a programmable heat block (Perkin Elmer Cetus Instruments, Norwalk, Conn.). The total time required for the PCR reaction was 3–5 hours. The products of the reaction were characterized by agarose gel electrophoresis of samples (7 to 20 µl) followed by detection of amplified DNA with ethidium bromide staining.

B. Hybridization of Oligonucleotides

Aliquots of the reaction mixture were denatured by incubation in 0.4M NaOH, 0.6M NaCl for five min., then neutralized by addition of two volumes of 1M Tris-HCl, pH 7.0 and applied to Genescreen Plus Membranes (New England Nuclear, Boston, Mass.) using a slot blot apparatus (Schleicher and Schuell, Keene, N.H.). Membranes were baked at 80° C. for 15 min. $^{32}$P-labeling of oligonucleotides, (According to Maniatis et. al., Molecular Cloning, Cold Spring Harbor Laboratory (198) p122–123.), and hybridization, washing of membranes, and autoradiography were performed as described in Wood, et. al., 1985, *Proc. Natl. Acad. Sci USA* 82:1585–1588, except for the following minor modifications. Filters were prehybridized in 5× Denhardts (1× Denhardts is 0.2 mg/ml each albumin, polyvinylpyrrolidone, and Ficoll), 5× SSC (1× SSC is 0.15M NaCl, 0.015M Na citrate, pH 7.0), 10 mM Na phosphate, and 5 mM EDTA for 1–3 hours at 68° C. Filters were hybridized overnight in 5× SSC, 10× Denhardt's, 20 mM Na phosphate, 100 µg/ml herring DNA, 5 mM EDTA, 7% SDS and 0.5–1.1×10$^6$ cpm/ml oligonucleotide probe. Total processing time from receipt of samples to development of autoradiograms can be two days.

C. Selection and nomenclature of probes

Sequences used for creating oligonucleotide probes were derived by comparison with sequences for known alleles. A sequence conserved in all alleles was used to prepare a control probe. The sequences of all known alleles were aligned and regions chosen to identify individual alleles. Some alleles, particularly DR beta alleles, do not contain a unique sequence and must be identified with a combination of probes that detect sequences present in two or more alleles. The oligonucleotide probes used here are listed in Table 7:

TABLE 7

| PROBE NAME | PROBE SEQUENCE |
|---|---|
| | DR Locus |
| E 58 | 5'-GCCTGATGAGGAGTACTGG |
| L 30 | 5'-CTGGAAAGACTCTTCTATA |
| D 70.1 | 5'-CTGGAAGACAGGCGGGCCG |
| H 30 | 5'-CTGGAGAGACAC |
| F 37 | 5'-GGAGTTCGTGCG |
| DE 70 | 5'-CTGGAAGACGAGCGGGCCG |
| FL 37 | 5'-GGAGTTCCTGCG |
| A 70 | 5'-CTGGAGCAGGCGCGGGCCG |
| H 33 | 5'-TACTTCTATCACCAAGAGG |
| N 77 | 5'-GGACAACTACTG |
| ErCV 28 | 5'-CTGGAAAGATGCATCTATA |
| N1I26 | 5'-GGAACCTGATCA |
| dsdvge 41 | 5'-GACAGCGACGTGGGGGAG. |
| | DQ Locus |
| E 45 | 5'-GGAGGTGTACCG |
| EF 46 | 5'-GGGGGAGTTCCG |
| iynre 31 | 5'-CTATAACCGAGA |
| | B Locus |
| A 46 | 5'-CGAGGATGGCGCCCCGGGC |
| egpeyw 55 | 5'-GGAGGGGCCGGAGTATTGG |

The oligonucleotide probes are named according to the corresponding amino acid sequences using single letter symbols. Consensus probes are named in lower case letters. The DR-B consensus sequence is named "dsdvge". Polymorphic probes are designated by upper case letters symbolizing the residue(s) that differ(s) from the consensus sequence followed by a number indicating the position of the first polymorphic residue in the name of the probe. For example, the probe "E 58" encodes the consensus sequence with the exception of the glutamic acid (E) codon at position 58. The polymorphic probes can be associated with one or a few HLA-DR alleles as indicated by comparison of nucleic acid sequences. When a single serological specificity is associated with multiple nucleic acid sequences, the alleles are given the serological designation followed by a lower case letter (e.g., DRw11a and DRw11b).

HLA-deficient severe combined immunodeficiency (SCID) is a rare disorder characterized by combined immunodeficiency associated with defective expression of class I and/or class II HLA products on mononuclear cells. Early reports described this disorder as bare-lymphocyte syndrome (Touraine, et al., 1985, *Exp. Hematol.* 13(Suppl 17):86–87). However, recently the term "HLA-deficient SCID" has been used to acknowledge the presence of non-HLA proteins on the surface of mononuclear cells. Without correction of the disorder, the immunodeficient patient will succumb to overwhelming infection, usually during the first few years of life. Although bone marrow transplantation is the treatment of choice, donor selection is impeded by the inability to use standard serological methods to determine the patient's HLA type.

Diagnosis of HLA-deficient SCID was based on the infant subject's immunodeficiency manifested by a progressive pneumonia due to Pneumocystis carinii, absence of serum immunoglobulins and lack of expression of human lymphocyte antigens on the mononuclear cells. The HLA deficiency was indicated by the lack of HLA on the cell surface (by FACS analysis using anti-beta 2 microglobulin and anti-DR monoclonal antibodies) and failure to detect class I or class II antigens by serological typing methods. Initially, HLA typing of the patient samples was completely negative except for weak reactions with two of six HLA-A2 antisera. After culturing cells with a variety of mitogen and lymphokines, HLA-B, -DR, and -DQ loci were not detectable.

The HLA -DR, -DQ, and -B types of the subject were determined by SSOPH of amplified DNA. Polymorphic regions of the HLA genes were amplified from genomic DNA using the primers described in Table 6. Electrophoretic analysis of the products of each amplification revealed a single ethidium bromide staining band of predicted size (data not shown). Amplified DNA, from case samples and a control panel, was analyzed by sequence-specific oligonucleotide probe hybridization (SSOPH) with the probes listed in Table 7.

Oligonucleotide probes were designed to detect polymorphisms that are associated with HLA phenotypes that would be expected in the patient, based on serological analysis of samples from family members. The relevant HLA-DR types detected in family members were HLA-DR2, 4(w53), 7(w53), and w11(w52). A preliminary SSOPH for DR2, 4, 7, w11 and w52 indicated that the subject was DR7, w11, w52.

The HLA-DR region of the major histocompatibility complex of DR7 and DRw11 individuals usually contains two loci encoding DR beta chains. The DR 7 and DRw11 products are encoded by the B1 locus, and the supertypic specificities DRw52 and DRw53 are encoded by the B3 and B4 loci, respectively. There are several different B1 locus sequences that can give rise to a HLA-DRw11 serotype and several different B3 sequences that are associated with the DRw52 specificity.

A second level of SSOPH provided discrimination between the three possible types of HLA-DRw11 sequences and three possible DRw52 sequences. The resulting hybridization pattern was consistent with the presence of sequences derived from cell lines that were typed as DRw11a and DRw52b. SSOPH was also utilized to confirm the presence of anticipated alleles of HLA-DRw53, HLA-B (B13) and HLA-DQ (DQw2 and DQw7).

SSOPH data are shown in FIG. 1. The subject row (child) shows positive hybridization with three polymorphic probes, D 70, E 58 and L 30. Positive hybridization of the E 58 probe is consistent with the presence of a DRw11 allele. The specificity of hybridization of the E 58 probe is demonstrated in the experimental control shown in FIG. 2. E 58 hybridizes to DNA from a homozygous DRw11 cell line but does not hybridize to DNA derived from a control panel of cells expressing other HLA-DR alleles.

The presence of a DRw11 subtype in the subject is also indicated by hybridization with the D 70 probe. This probe hybridizes with HLA-DRw8 and with the -DRw11a allele (see FIG. 2), thus indicating that the patient is DRw11a. This allele is also present in the patient's father and paternal grandfather. A similar process can be used to interpret the hybridization results using the other two probes. Probe L 30 hybridization with patient and maternal DNA indicates the presence of DR 7. The A 70 probe indicates the presence of an HLA -DR2 allele which is detected in the aunt, half-sibling, maternal grandmother, and paternal grandmother.

As shown in FIG. 2, all hybridization experiments include controls to confirm the specificity of hybridization. A summary of the hybridization data from the HLA-DR, -DQ, and -B loci is as follows:

TABLE 8

| PROBE | C | M | F | mGM | mGF | pGM | pGF | 1/2S | A | D1 | D2 | ASSOCIATION |
|---|---|---|---|---|---|---|---|---|---|---|---|---|
| DR Locus | | | | | | | | | | | | |
| E 58 | + | − | + | − | − | − | + | − | − | + | + | DR5(w11) |
| L 30 | + | + | − | − | + | − | − | − | − | + | + | DR7 |
| D70.1 | + | − | + | − | − | − | + | − | − | + | + | DR5(w11),DR8 |
| H30 | + | − | + | − | − | − | + | − | − | + | + | DRw52b |
| F 37 | + | + | − | − | + | − | − | − | − | − | + | DR7,DRw52c,DR6Dw9 |
| DE 70 | − | − | − | + | − | − | − | − | − | − | − | DR6(w13);DR4Dw10;DRw11b |
| FL 38 | − | − | − | + | − | − | + | − | − | − | − | DRw52a |
| ErCV 28 | − | − | − | − | − | − | − | + | − | − | − | DR1 |
| A 70 | − | + | − | + | + | + | − | + | + | − | − | DR2(w15,w16) |
| N 77 | − | − | − | − | − | − | + | − | − | − | − | DR3 |
| H 33 | − | − | + | − | − | + | − | − | − | − | − | DR4 |
| N11 26 | + | + | + | − | + | + | − | − | − | + | + | DRw53 |
| dsdvge 41 | + | + | + | + | + | + | + | + | + | + | + | DRbeta |
| DQ Locus | | | | | | | | | | | | |
| E 45 | + | − | + | n | − | + | + | n | n | + | − | DQw7 |
| EF 46 | + | + | − | n | + | − | + | n | n | + | + | DQw2 |
| iynre 31 | + | + | + | n | + | + | + | n | n | + | + | DQbeta |
| B Locus | | | | | | | | | | | | |
| A 46 | + | + | − | − | + | − | − | − | − | + | + | B13 |
| egpeyw 55 | + | + | + | + | + | + | + | + | + | + | + | A and B |

The source of the samples is listed across the top (C-patient; M-mother; F-father; mGM-maternal grandmother; mGF-maternal grandfather; pGM-paternal grandmother; pGF-paternal grandfather; ½S-half sibling; A-aunt, and D1 and D2-unrelated donors). The probes for each locus are indicated at the left. The association of each probe with HLA alleles is shown at the right.

The best match was between the patient and the two unrelated potential donors. With the probes used, potential unrelated donors D1 and D2 showed an identical polymorphism profile for HLA-DR, but only Donor D1 was identical for all three loci. Combining the patient and family data, the class II haplotypes of the patient were deduced as DRw11a(w52b); DQw7/DR7(w53); DQw2.

Samples from the subject's family members were typed by both serological and SSOPH methods. The oligonucleotide hybridization data correlated perfectly with the HLA types identified serologically, as shown in the the follwing Table 9:

TABLE 9

|   | Serology | SSOPH DR | Partial DQ | B13 |
|---|---|---|---|---|
| a | A2;B35(w6);Cw4, DRw11(w52),DQw7 | E58,DE70,H30 | E45 | |
| b | A26;B41(w6);Cw-, DR4(w53),DQw7 | H33,N1126 | E45 | |
| c | A2;B35(w6);Cw4; DRw15,DQw1 | A70 | | |
| d | A2,B13(w4);Cw6, DR7(w53);DQw2 | L30,F37,N1126 | EF46 | A46 |
| e | A31;B60(w6);Cw3, DR3(w52);DQw2 | FL37,N77 | EF46 | |
| f | A24;B44(w4);Cw-; DRw15,DQw1 | A70 | | |
| g | A2:B7(w6);Cw7; DRw15,DQw1 | A70 | | |
| h | A24;B44(w4);Cw; DRw13(w52);DQw1 | FL37,DE70 | | |

Serological specificities (top left) and SSOPH (top right) are indicated for each haplotype derived from the pedigree of the patient's family. FIG. 3 illustrates schematically that the patient (bottom circle) inherited types a,d from respective parents.

The serological typing of the patient's family and analysis of the segregation of human lymphocyte antigen allowed determination of the haplotypes of the patient's family. None of the family members were HLA-identical to the patient. As a result, a search for a well-matched unrelated donor was initiated. The search revealed two potential donors who were HLA-typed by both serological and SSOPH methods. This information was utilized to select the best possible donor for transplantation. The serological typing of the selected donor (D1) was A2, 11; B13, 35, (w4, 6); DR7, w11, (w52, w53); DQw2, w7, and the SSOPH pattern was associated with B13; DR7, w11a, w52b, w53; DQw2, w7 (Table 8).

The patient was transplanted and engrafted readily as determined by chromosomal analysis, normal class I and II HLA expression, and detection of HLA-A11. The patient was alive and infection free 21 months following transplantation.

We claim:

1. A method for selecting a donor for purposes of bone marrow transplantation from the donor to a recipient, which comprises determining the HLA type of the recipient, determining the HLA type of one or more potential donors, and selecting the donor having an HLA type most similar to the recipient, wherein the improvement comprises:

(A) determining if the recipient's HLA-DR allele(s) correspond(s) to an allele selected from the group consisting of HLA-DRw52c, DR12a,b, DR3a,b, DR5a–e, DRNew1, DR6a–e, DR8a–d, DRw53a–c, DR4a–f, DR7, DR9, DR2a–c B3, DR2a–d B1, DR10, and DR1a–c;

(B) determining if each donor's HLA-DR allele(s) corresponds to an allele selected from the group; and (C) selecting the donor having HLA-DR allele(s) that most closely match the recipient.

2. In a method of HLA typing which includes the steps of determining the HLA type of a tissue sample and comparing the result with known HLA types, the improvement which comprises: determining if the tissue sample is HLA, DR8d, DR12a–b, DR1b–c or DRw52c.

3. The method of claim 1, wherein the improvement further comprises determining if the recipient has HLA-DR allele HLANew1, and if a positive result is obtained, determining if each donor is HLANew1.

4. The method of claim 1, wherein the improvement further comprises determining if the recipient has HLA-DR allele HLA DR8d, and if a positive result is obtained, determining if each donor is HLA DR8d.

5. The method of claim 1, wherein the improvement further comprises determining if the recipient has HLA-DR allele HLA-DR12a, and if a positive result is obtained, determining if each donor is HLA DR12a.

6. The method of claim 1, wherein the improvement further comprises determining if the recipient has HLA-DR allele HLA-DR12b, and if a positive result is obtained, determining if each donor is HLA DR12b.

7. The method of claim 1, wherein the improvement further comprises determining if the recipient has HLA-DR allele HLA-DR1b, and if the a positive result is obtained, determining if each donor is HLA-DR1b.

8. The method of claim 1, wherein the improvement further comprises determining if the recipient has HLA-DR allele HLA-DR1c, and if the a positive result is obtained, determining if each donor is HLA-DR1c.

9. The method of claim 1, wherein the improvement further comprises determining if the recipient has HLA-DR allele HLA-DRw52c, and if a positive result is obtained, determining if each donor is HLA-DRw52c.

10. The method of claim 1, wherein the improvement further comprises determining if the recipient has an HLA-DR allele selected from the group consisting of HLA-DR8d, DR12a, DR12b, DR1b, DR1c, DRw52c and DRNew1, and if a positive result is obtained, determining if each donor has the HLA-DR allele so determined.

11. The method of claim 2, wherein the determining step further comprises determining if the tissue sample is HLA DR8d.

12. The method of claim 2, wherein the determining step further comprises determining if the tissue sample is HLA DR12a.

13. The method of claim 2, wherein the determining step further comprises determining if the tissue sample is HLA DR12b.

14. The method of claim 2, wherein the determining step further comprises determining if the tissue sample is HLA DR1b.

15. The method of claim 2, wherein the determining step further comprises determining if the tissue sample is HLA DR1c.

16. The method of claim 2, wherein the determining step further comprises determining if the tissue sample is HLA DRw52c.

* * * * *